(12) United States Patent
Burman et al.

(10) Patent No.: US 6,596,755 B2
(45) Date of Patent: Jul. 22, 2003

(54) ORAL FORMULATION OF METHYLGLYOXAL AND ITS IMINO ACID CONJUGATES FOR HUMAN USE

(75) Inventors: Anand C. Burman, Regents Park (GB); Rama Mukherjee, Gurgaon (IN); Dhiraj Khattar, Ghaziabad (IN); Mukesh Kumar, Delhi (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

(21) Appl. No.: 10/187,422

(22) Filed: Jul. 1, 2002

(65) Prior Publication Data

US 2003/0087951 A1 May 8, 2003

Related U.S. Application Data

(60) Provisional application No. 60/302,631, filed on Jul. 2, 2001.

(51) Int. Cl.[7] .............................................. A61K 31/40
(52) U.S. Cl. ........................ 514/423; 514/424; 514/675; 514/693
(58) Field of Search ................................ 514/423, 424, 514/675, 693

(56) References Cited

U.S. PATENT DOCUMENTS 5,147,652 A * 9/1992 Egyud ........................ 424/450

OTHER PUBLICATIONS

Golej, J. et al., "Oral administration of methylglyoxal leads to kidney collagen accumulation in the mouse", abstract of Life Sciences, 63(9), pp. 801–807, 1998.*

* cited by examiner

Primary Examiner—Dwayne C. Jones
(74) Attorney, Agent, or Firm—Ladas & Parry

(57) ABSTRACT

The invention relates to an oral formulation of methylglyoxal and/or its imino acid conjugates for human use and methods for preparing the compositions. Particularly, the invention relates to compositions comprising methylglyoxal and more particularly, imino acid conjugates of methylglyoxal. The present invention also relates to formulations of methylglyoxal and imino acid conjugates of methylglyoxal that can be used for the treatment and suppression of malignant diseases including but not limited to the cancers of Colon, Prostate, Pancreas, Lung, Oral cavity, Glioblastoma, and Leukemia.

14 Claims, No Drawings

ORAL FORMULATION OF METHYLGLYOXAL AND ITS IMINO ACID CONJUGATES FOR HUMAN USE

This application claims the benefit of U.S. Provisional Application(s) No(s).: 60/302,631 filed Jul. 2, 2002.

FIELD OF THE INVENTION

The invention relates to an oral formulation of methylglyoxal and/or its imino acid conjugates for human use and methods for preparing the compositions. Particularly, the invention relates to compositions comprising methylglyoxal and more particularly, imino acid conjugates of methylglyoxal. The present invention also relates to formulations of methylglyoxal and imino acid conjugates of methylglyoxal that can be used for the treatment and suppression of malignant diseases including but not limited to the cancers of Colon, Prostate, Pancreas, Lung, Oral cavity, Glioblastoma, and Leukemia.

BACKGROUND OF THE INVENTION

Alpha-ketoaldehydes are a series of chemicals derived from glyoxal (CHO—CHO), a dialdehyde with two carbon atoms. Methylglyoxal (2-oxopropanal) is the simplest alpha-ketoaldehyde that occurs naturally in small quantities inside normal cells. It is continually formed from several metabolic sources. Within a cell, alpha-ketoaldehydes function in regulating cell division [1]

Methylglyoxal ($CH_3COCHO$), with three carbon atoms (C-3), is the first member of an aliphatic series where each consecutive member is extended by a $CH_2$ unit (i.e., C-4, ethylglyoxal $CH_3$—$CH_2$—CO—CHO; C-5, propylglyoxal $CH_3$—$CH_2$—$CH_2$—CO—CHO; etc.)

Methylglyoxal is a normal cellular metabolite with potential anticancer properties.

Szent-Gyorgyi and his collaborators in their pioneering work on the biological role of methylglyoxal had put forward strong evidences of in vitro inhibitory effect of methylglyoxal on Sarcoma-180 cells [2]. Egyud and Szent-Gyorgyi showed that when methylglyoxal was injected into mice along with sarcoma 180 cells, no tumor developed and mice remained completely healthy [3]. Apple and Greenberg similarly demonstrated that methylglyoxal significantly inhibited sarcoma tumor growth [4,5].

High concentrations of exogenous methylglyoxal exhibit selective inhibitory activity toward rapidly proliferating tumor cells versus non-proliferating normal cells in vitro. The molecular basis of methylglyoxal toxicity is not clearly understood, but may involve inhibition of DNA and protein synthesis [6,7]. Indeed, methylglyoxal is known to form adducts with nucleic acids. Additionally Methylglyoxal specifically inhibits mitochondrial respiration and glycolysis in a wide variety of malignant cells, whereas the respiration in normal cells remains uneffected by it under identical conditions [8]. This effect of methylglyoxal is mediated via an inactivation of the enzyme glyceraldehyde-3-phosphate dehydrogenase, a key glycolytic enzyme, reported to be structurally and functionally altered in malignant cells [9]. Methylglyoxal specifically inhibits electron flow through Complex 1 of the mitochondrial respiratory chain of and inactivates the enzyme glyceraldehyde 3 phosphate dehydrogenase, to mediate a critical reduction in the intracellular levels of ATP, leading to the inhibition of respiration in malignant cells [10].

By using a model malignant cell, the Ehrlich ascites carcinoma (EAC) cell developed in mice, Halder et al have further shown that methylglyoxal inhibits both mitochondrial respiration and glycolysis in this type of cells [11]. As a consequence of inhibition of both mitochondrial respiration and glycolysis ATP levels in these cells have been found to be critically reduced, rendering the cells non-viable.

Methylglyoxal is a very reactive and unstable molecule and tends to oxidise/polymerise on exposure to air. However, aqueous solutions of methylglyoxal at a concentration of 40% w/v or less are relatively stable. It is due to this reason that commercially available methylglyoxal is a 40% solution in water.

Much work has been carried out on the conjugates of methylglyoxal. U.S. Pat. No. 4,066,650 discloses the addition products between ketoaldehydes and secondary amines. The patent describes method of preparation of the addition products and the pharmaceutical compositions for the treatment of cancer. U.S. Pat. No. 4,238,500 describes the novel condensation products of α-ketoaldehyde with enediol and their pharmaceutical uses as anticancer, antihypotensive and analgesic compounds. U.S. Pat. No. 5,147,652 describes the liposome encapsulated ketaoaldehydes and their pharmaceutical use for the treatment of cancer and other non-self cells. U.S. Pat. No. 5,849,783 describes the physically and chemically latentiated methylglyoxal or α-ketoaldehydes for treating the non-self cells which includes cancer.

However, in order to study the effect of methylglyoxal in human patients suffering with cancer there is a need to develop a convenient formulation that is user friendly.

To date, there is no formulation reported for the administration of methylglyoxal for human use.

There is a need, therefore, for formulating methylglyoxal into pharmaceutically acceptable composition(s) which can be conveniently given to cancer patients.

An aspect the present invention is to convert aqueous solution of methylglyoxal to a form that can be administered to cancer patients without losing its efficacy.

Another aspect of the present invention is to convert aqueous solution of methylglyoxal to a stable, solid form that can be used to administer methylglyoxal to cancer patients without losing its efficacy.

Another aspect of the present invention to formulate the imino acid conjugates of methylglyoxal into pharmaceutically acceptable composition(s) which can be conveniently given to cancer patients.

SUMMARY OF THE INVENTION

The present invention aims to present a formulation of methylglyoxal which can be given orally to cancer patients.

The present invention also aims to present formulations of imino acid conjugates of methylglyoxal which can be given orally to cancer patients.

DETAILED DESCRIPTION OF THE INVENTION

In the present invention imino acid refers only to pyroglutamic acid. Alkyl and aryl are defined below as substituent $R_1$. The general formula of these conjugates and pharmaceutically acceptable salts can be described as shown in the following structure (I)

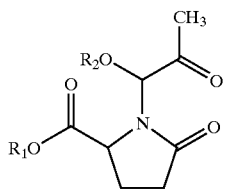

Structure (I)

where $R_1$ is any $C_1$–$C_{12}$ straight or branched alkyl group benzyl, or phenyl;

where $R_2$ is H, or $COR_3$ where $R_3$ is any $C_1$–$C_6$ straight or branched alkyl group, benzyl or phenyl.

The invention provides a process for the synthesis of alkyl/aryl ester of pyroglutamic acid, said process comprising:

(a) mixing of pyroglutamic acid, potassium hydrogensulphate and alcohol;

(b) heating the mixture in Microwave (MW) oven with intermittent stirring or heating the mixture to reflux with benzene as co-solvent with continuous stirring;

(c) monitoring the progress of the reaction by TLC;

(d) diluting the reaction mixture with ethyl acetate and filtering out the solid mass (e) evaporating the solvent to yield a colourless oil:

(f) purifying by silica gel column chromatography.

The invention also provides a process for preparing a conjugate of methyl glyoxal with alkyl/aryl pyroglutamate, said process comprising:

(a) mixing of alkyl/aryl pyroglutamate, methyl glyoxal and optionally bentonite or clay in Dioxan:water:2:1;

(b) heating the mixture in MW oven with intermittent stirring or heating to reflux with continuous stirring;

(c) monitoring the reaction by TLC;

(d) diluting the mixture with MeOH and filtering;

(e) concentrating the filtrate in Rotovapor;

(f) removing the residual water as an azeotropic mixture with ethyl acetate;

(g) purifying by silica gel column chromatography.

The invention also provides a process for preparing acetate of the conjugate of methyl glyoxal-alkyl/aryl pyroglutamate, said process comprising:

(a) sonicating a mixture of conjugate of methyl glyoxal-alkyl/aryl pyroglutamate, acetic anhydride and bentonite or clay;

(b) monitoring the reaction by TLC;

(c) diluting with chloroform and filtering the mixture;

(d) concentrating the filtrate in vacuo to yield a crude oily substance;

(e) purifying by silica gel column chromatography.

Other methods known in the art can be used to prepare the imino acid conjugates of methylglyoxal of formula I.

Pharmaceutically salts of the imino acid conjugates include the but are not limited to the following: acetate, ascorbate, benzoate, citrate, oxalate, stearate, trifluroacetate, succinate, tartarate, lactate, fumarate, gluconate, glutamate, phosphate/diphosphate, and valerate. Other salts include Ca, Li, Mg, Na, and K salts, halides, salts of amino acids such as lysine or arginine; guanidine, ammonium, substituted ammonium salts or aluminium salts. The pharmaceutically acceptable salts of the imino acid conjugate may be prepared by methods known in the art.

The more preferred methylglyoxal conjugates (MGC) are listed as below:

[MGC-1]

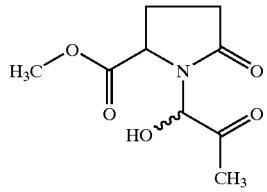

N-(1-hydroxy-2-ketopropyl)-methylpyroglutamate

[MGC-2]

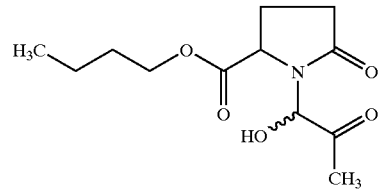

N-(1-hydroxy-2-ketopropyl)-butylpyroglutamate

[MGC-3]

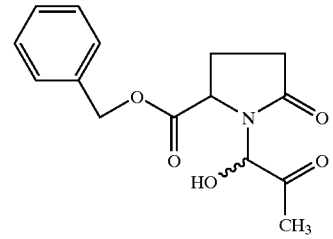

N-(1-hydroxy-2-ketopropyl)-benzylpyroglutamate

[MGC-4]

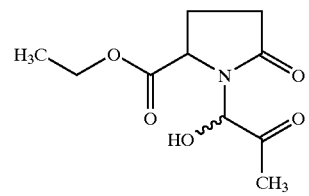

N-(1-hydroxy-2-ketopropyl)-ethylpyroglutamate

[MGC-5]

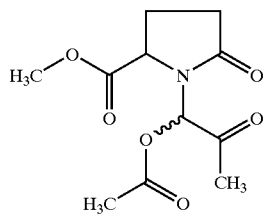

N-(1-acetoxy-2-ketopropyl)-methylpyroglutamate

[MGC-6]

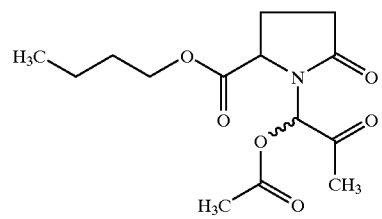

N-(1-acetoxy-2-ketopropyl)-butylpyroglutamate

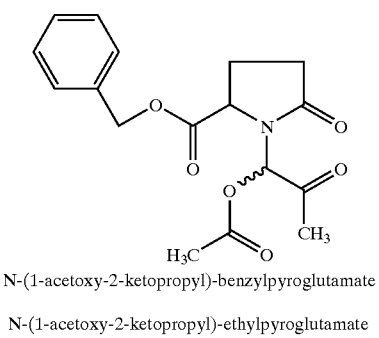

N-(1-acetoxy-2-ketopropyl)-benzylpyroglutamate [MGC-7]

N-(1-acetoxy-2-ketopropyl)-ethylpyroglutamate [MGC-8]

The present invention provides compositions and methods for the presentation of methylglyoxal and/or its imino acid conjugates in pharmaceutically acceptable form for oral administration to cancer patients. In the compositions of this invention methylglyoxal and/or its imino acid conjugates remain physically and chemically stable and can be administered in various dosage forms at a drug dose meant to be effective to exhibit clinically significant anticancer activity.

The methods of this invention comprise, consist of, or consist essentially of administering orally to the mammal a therapeutically effective formulation of methylglyoxal or imino acid conjugates of methylglyoxal. An effective dose of methylglyoxal or its conjugates or pharmaceutically acceptable salts therof ranges from 1 mg/Kg. B. Wt to 300 mg/Kg. B. Wt (preferably 10–100 mg)/Kg. B. Wt) of the mammal, with the dose dependent on the effects sought, the manner of administration, and the cancer being treated). In accordance with good clinical practice, it is preferred to administer the formulation at a dose that will produce anticancer effects without causing undue harmful side effects. The formulation may be administered either alone or as a mixture with other therapeutic agents such as 5-fluorouracil, methotrexate, etoposide, paclitaxel, taxotere, doxorubicin, daunarubicin, vincristine, vinblastine and other such known and established anticancer drugs.

Methylglyoxal and/or its imino acid conjugates can be administered orally to human cancer patients simply by diluting with purified water to form a solution.

Methylglyoxal and/or its conjugates can be administered orally to human cancer patients by incorporating in a flavoured/sweetened syrup base.

Solution of methylglyoxal and/or its conjugates can be adsorbed onto inert excipients like colloidal silica to convert into a solid form for ease of administration.

Methylglyoxal solution or solution of imino acid conjugates of methylglyoxal can be lyophilized with the incorporation of cryoprotective agents exemplified by but not limited to mannitol, lactose, sorbitol, trehalose etc.

The lyophilized or the adsorbed form of methylglyoxal and/or its conjugates is the most suitable and user friendly form that can be dispensed in a sachet, ampoule, vial, filled into hard gelatin capsules or into soft gelatin capsules or compressed into tablets with or without the addition of excipients.

All the above delivery systems may contain added auxiliary agents such as filler, diluents, preservatives, stabilizers etc.

The unit dosage ranges from 60 mg to 18 gm, more preferably 600mg to 6 gm.

The present invention will now be illustrated by the following examples, which are not intended to be limiting in any way.

EXAMPLE 1

Preparation of Lyophilized Methylglyoxal 13.8 gm of Mannitol was dissolved in 100 ml of purified water and 3 ml of methylglyoxal solution (40%) was added to it. The solution was then lyophilized to obtain a dry powder. Each 12.5 gm of this powder contains 1 gm of methylglyoxal.

The quantity of mannitol per 100 ml of purified water can vary from 2 gm to 50 gm. However, best lyophilized cake was obtained for mannitol concentrations between 7 gm to 20 gm per 100 ml of purified water. Quantity of methylglyoxal can vary from 1 ml to 50 ml depending on the requirement.

EXAMPLE 2

Preparation of Lyophilized Preparations of Imino Acid Conjugates of Methylglyoxal 13.8 gm of Mannitol was dissolved in 100 ml of purified water and 3 ml solution of imino acid conjugate of methylglyoxal (approx 40% ethanolic soln.) was added to it. The solution was then lyophilized to obtain a dry powder. Each 12.5 gm of this powder contains 1 gm of conjugate of methylglyoxal.

The quantity of mannitol per 100 ml of purified water can vary from 2 gm to 50 gm. However, best lyophilized cake was obtained for mannitol concentrations between 7 gm to 20 gm per 100 ml of purified water. Quantity of methylglyoxal can vary from 1 ml to 50 ml depending on the requirement.

EXAMPLE 3

Comparative In-vitro Cytotoxicity of Methylglyoxal and Imino Acid Conjugates of Methylglyoxal The formulation of Methylglyoxal and its imino acid conjugates were tested for cytotoxicity against 7 human tumor cell lines and the cytotoxicity values were compared with their respective DMSO controls, which served as Standards. Briefly, a three day MTT cytotoxicity assay was performed, which is based on the principle of uptake of MTT (3-(4,5-dimethylthiazol-2-yl)-2,5-diphenyl tetrazolium bromide), a tetrazolium salt, by the metabolically active cells where it is metabolized by active mitochondria into a blue colored formazan product that is read spectrophotometrically. MTT was dissolved in phosphate buffered saline with a pH of 7.4 to obtain an MTT concentration of 5 mg/ml; the resulting mixture was filtered through a 0.22 micron filter to sterilize and remove a small amount of insoluble residue. For each type of tumor cell, 20,000 to 50,000 cells were seeded in a 96-well culture plate and incubated with the formulation or standard in a $CO_2$ incubator for 24 hours. The final concentration range of methylglyoxal and its conjugates was 1 to 10 mM. Control cells not treated with methylglyoxal or its conjugates were similarly incubated. The assay was terminated after 72 hours by adding 100 ug (20 ul) of MTT to each well, then incubating for additional one hour, and finally adding 50 ul of 10% SDS-0.01N HCl to each well to lyse the cells and dissolve formazan. After incubating for one hour, the plate was read spectrophotometrically at 540 nm and the percentage cytotoxicity calculated. Table-I compares the $ED_{50}$ values of methylglyoxal Standard with methylglyoxal formulation and Table-II compares the $ED_{50}$ values of Standard of methylglyoxal conjugates with the formulation of methylglyoxal conjugates.

There was no significant difference in $ED_{50}$ values for cytotoxity between either methylglyoxal Standard and methylglyoxal formulation or Standard of methylglyoxal conjugates and methylglyoxal conjugate formulation.

TABLE I

Comparison Of $ED_{50}$ Values Of Cytotoxicity Of Standard And Formulation Of Methylglyoxal Against Various Human Tumor Cell Lines

|  |  | Methylglyoxal ($ED_{50}$ in mM) | |
|---|---|---|---|
| S. NO | CELL LINE | Standard | Formulation |
| 1 | U87MG Glioblastoma | 1.95 ± 0.7 | 1.80 ± 0.7 |
| 2 | KB Oral | 0.9 ± 0.2 | 0.8 ± 0.1 |
| 3 | PTC Colon | 0.7 ± 0.1 | 0.8 ± 0.1 |
| 4 | DU145 Prostate | 1.5 ± 0.6 | 1.6 ± 0.4 |
| 5 | Miapaca2 Pancreas | 0.7 ± 0.1 | 0.6 ± 0.2 |
| 6 | L132 Lung | <1.0 | 1.0 ± 0.1 |
| 7 | Molt 4 Leukemia | 0.8 ± 0.2 | 0.85 ± 0.2 | centrifuged at 10,000 rpm for 10 minutes. The supernatent was pipetted out and discarded. The residual precipitate was dissolved in 1 ml of THF (tetrahydrofuran) and the final volume was made up to 1.5 ml with acetonitrile. The resultant solution was analysed by using following HPLC conditions.

| Chromatographic Conditions | |
|---|---|
| Column | Lichrospher RP18e (250 - 4,5 $\mu$) |
| Mobile Phase | Water:Acetonitrile (35:65) |
| Detection | UV - 430 nm |
| Injection Volume | 20 $\mu$l |
| Flow Rate | 1.5 ml/minute |
| Temperature | 35° C. |

The method was found to be linear over the concentration range of 10 $\mu$g/ml to 200 $\mu$g/ml. The specificity of the method was verified by evaluating the retention times of hydrazones of different keto-aldehydes i.e. acetone and acetaldehyde which were found to be well resolved using the method specified. No interference was observed due to mannitol in the lyophilized methylglyoxal sample. The precision and accuracy of the method w.r.t. methylglyoxal was also validated.

TABLE II

Comparison Of $Ed_{50}$ Values Of Cytotoxicity Of Standard And Formulation Of Methylglyoxal Conjugates Against Various Human Tumor Cell Lines

| | | $ED_{50}$ (mM) | | | | | | | |
|---|---|---|---|---|---|---|---|---|---|
| | | MGC1 | | MGC4 | | MGC7 | | MGC8 | |
| S. No | CELL LINE | Standard | Formulation | Standard | Formulation | Standard | Formulation | Standard | Formulation |
| 1 | U87MG Glioblastoma | 2.25 ± 0.5 | 2.4 ± 0.3 | 2.4 ± 0.5 | 2.2 ± 0.5 | 1.84 ± 0.6 | 2.0 ± 0.6 | 1.88 ± 0.7 | 2.0 ± 0.1 |
| 2 | KB Oral | 1.7 ± 0.5 | 1.5 ± 0.3 | 1.55 ± 0.3 | 1.9 ± 0.4 | 1.85 ± 0.6 | 1.6 ± 0.3 | 1.95 ± 0.8 | 1.5 ± 0.0 |
| 3 | PTC Colon | 3.7 ± 1.4 | 3.3 ± 0.7 | 3.8 ± 1.1 | 3.6 ± 1.0 | 2.4 ± 0.5 | 2.2 ± 0.8 | 2.75 ± 0.4 | 2.6 ± 0.6 |
| 4 | DU145 Prostate | 1.7 ± 0.6 | 1.5 ± 0.2 | 1.8 ± 0.3 | 1.4 ± 0.7 | 0.85 ± 0.3 | 0.9 ± 0.1 | 1.3 ± 0.3 | 1.0 ± 0.1 |
| 5 | Miapaca2 Pancreas | 4.2 ± 1.3 | 4.0 ± 1.0 | 4.2 ± 1.1 | 4.6 ± 1.1 | 2.4 ± 1.0 | 2.3 ± 0.8 | 1.8 ± 0.9 | 1.9 ± 0.7 |
| 6 | L132 Lung | >5 | >5 | >5 | >5 | >5 | >5 | >5 | >5 |
| 7 | Molt 4 Leukemia | 1.5 ± 0.4 | 1.3 ± 0.7 | 1.5 ± 0.2 | 1.3 ± 0.1 | 1.5 ± 0.2 | 1.3 ± 0.2 | 2.9 ± 0.5 | 2.7 ± 0.8 |

EXAMPLE 4

Quntitative Estimation of Methylglyoxal

Methylglyoxal was quantitated by derivatizing it to a hydrazone and estimating this hydrazone using HPLC.

HPLC Method

Derivatization and Sample Preparation 2,4-Di-Nitro Phenyl Hydrazine (DNPH) was used for the derivatization of methylglyoxal. The reagent was prepared at a concentration of 0.2% in 2M HCl solution. In a 2 ml centrifuge tube 200 $\mu$l of methylglyoxal solution (80 $\mu$g/ml in water) and 200 $\mu$l of DNPH reagent (0.2% DNPH in 2M HCl) was taken and the mixture was vortexed and kept in a shaking water bath at 38°–40° C. for 30 minutes. The hydrazone of methylglyoxal was precipitated which was The stability indicating nature of the method was then checked by doing a stress stability study. MG (40% soln.) was exposed to $H_2O_2$ (strong oxidising agent) for different time intervals (10 min, 1.5 hrs, 4 hrs and 24 hrs) at 40° C. Methylglyoxal remaining (not degraded by $H_2O_2$) was then converted to hydrazone by the method developed above and quantitated by HPLC. Extent of degradation of methylglyoxal by $H_2O_2$ was found to be dependent on the time of exposure to $H_2O_2$. Methylglyoxal was found to be totally degraded by $H_2O_2$ in 24 hrs as this sample did not yield any hydrazone. No interference was observed due to degradation product as none of the degradation products formed hydrazone derivative. The peak obtained by the hydrazone of methylglyoxal in the degraded sample was checked for peak purity using a diode-array detector and was found to be absolutely pure.

EXAMPLE 5

Stability of Methylglyoxal Solution and Lyophilized Methylglyoxal

The accelerated stability of methylglyoxal solution (40%) and lyophilized methylglyoxal prepared in Example 1 was done using a stability indicating HPLC method of Example 4. The samples were kept at 4° C., 25° C./60% relative humidity (RH) and 40° C./75% RH as per ICH guidelines. The samples were analysed at regular time intervals i.e. 10 days, 20 days, 1 month, 2 months and 3 months for methylglyoxal content.

Data obtained till 3 months indicates no significant degradation at 25° C./60% RH and almost no degradation at 4° C., the recommended temperature for storage. At 40° C./75% RH (stress condition), degradation was found to be about 10%

EXAMPLE 6

Stability of Imino Acid Conjugates of Methylglyoxal (MGC-8)

The accelerated stability of MGC-8 formulation (prepared as per method mentioned in Example-2) was done using a stability indicating HPLC method of Example 4. The samples were kept at 4° C., 25° C./60% RH and 40° C./75% RH as per ICH guidelines. The samples were analysed at regular time intervals i.e. 10 days, 20 days, 1 month, 2 months and 3 months.

Data obtained till 3 months indicates no significant degradation at 25° C./60% RH and almost no degradation at 4° C, the recommended temperature for storage. At 40° C./75% RH (stress condition), degradation was found to be within 5%

EXAMPLE 7

Preparation of Lyophilized Methylglyoxal 13.8 gm of Lactose was dissolved in 100 ml of purified water and 3 ml of methylglyoxal solution (40%) was added to it. The solution was then lyophilized to obtain a dry powder. Each 12.5 gm of this powder contains 1 gm of methylglyoxal.

The quantity of lactose per 100 ml of purified water can vary from 5 gm to 20 gm. However, best lyophilized cake was obtained for lactose concentrations between 10 gm to 15 gm per 100 ml of purified water. Quantity of methylglyoxal can vary from 1 ml to 50 ml depending on the requirement.

EXAMPLE 8

Preparation of Capsules of Lyophilized Methylglyoxal

The lyophilized methylglyoxal powder obtained in Example 1 was mixed with excipients like lubricants and glidants exemplified by but not limited to talc, magnesium stearate, colloidal silica, etc. and filled into hard gelatin capsules.

EXAMPLE 9

Preparation of Capsules of MGC-3

N-(1-hydroxy-2-ketopropyl)-benzylpyroglutamate (MGC-3) was dissolved in ethanol. The ethanolic solution of MGC-3 was then adsorbed on to colloidal silicon dioxide and the solvent was evaporated. The dry powder obtained was mixed with excipients like lubricants and glidants exemplified by but not limited to talc, magnesium stearate, colloidal silica etc and filled into hard gelatin capsules.

EXAMPLE 10

Preparation of Soft Gelatin Capsules of MGC-6

N-(1-acetoxy-2-ketopropyl)-butylpyroglutamate (MGC-6) was dispersed in vehicles like PEG 400, mineral oil and encapsulated into soft gelatin capsules.

EXAMPLE 11

Preparation of Sachets of Lyophilized Methylglyoxal and its Imino Acid Conjugates The lyophilized powder of methylglyoxal or its conjugate obtained in Examples 1 or 2 respectively was mixed with excipients like dry flavours, lubricants and glidants exemplified by but not limited to colloidal silica and filled into sachets. Each sachet to be opened and the contents dissolved into drinking water at the time of taking the dose.

References

1. Egyud, Laszlo G., "Autobiotics and their use in eliminating nonself cells", U.S. Pat. No. 5,849,783, 1998
2. Szent-Gyorgyi, "Ciba Foundation Symposium", 67, 3–18 (1979)
3. Egyud, L. G. and Szent-Gyorgyi, A.; "Cancerostatic action of Methylglyoxal", Science, 160, 1140 (1968).
4. Apple and Greenberg, Cancer Chemother. Rep, 51, 455–464, (1967)
5. Apple and Greenberg, Cancer Chemother. Rep, 52, 687–696, (1968)
6. Conray P. J, ,Ciba Found Sympos, 67, 271–300, (1979)
7. Egyud, L. G. and Szent-Gyorgyi, "Proceed. Natl. Acad. Sci., USA, 56, 203–207, (1966)
8. Ray, M, Halder, J., Dutta, S. K. and Ray, S.; Int. J. Cancer, 47, 603–609, (1991).
9. Ray et al, Mol. and Cellular Biochem, 177, 21-26, (1997)
10. Ray et al, Biochem J, 303, 69–72, (1994)
11. Int J Cancer, 54, 443–449, (1993)

What is claimed is:

1. An oral formulation comprising an imino acid conjugate of methylglyoxal of Structure (I)

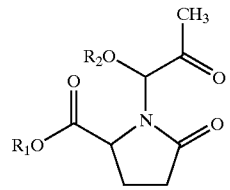

Structure 1 where $R_1$ is any ($C_1$–$C_{12}$) straight or branched alkyl group, benzyl, or phenyl;

where $R_2$ is H, or $COR_3$ where $R_3$ is any ($C_1$–$C_6$) straight or branched alkyl group, benzyl or phenyl or a pharmaceutically acceptable salt thereof.

2. The formulation according to claim 1, wherein the imino acid conjugate aqueous, solid or lyophilized form.

3. The formulation according to claim 1 in a dosage form selected from the group consisting of a solution, syrup, a sachet, a hard gelatin capsule, a soft gelatin capsule and a tablet.

4. The formulation according to claim 3, wherein a unit dosage ranges from 60 mg to 18 gm.

5. The formulation according to claim 1, which is cytotoxic to 7 human tumor cell lines selected from lung, pancreas, oral, glioblastoma, leukemia, colon and prostate tumor cells.

6. A method for treating cancer of the lung, colon, pancreas, oral, prostate, glioblastoma or lukemia comprising administering a formulation of an imino acid conjugate according to claim 1 to a patient in need thereof.

7. A method of treating cancer according to claim 6, by administering the formulation of an imino acid conjugate in the range of 1 to 300 mg/kg body weight of the patient.

8. The formulation according to claim 1, wherein the imino acid conjugate of methylglyoxal is selected from the group consisting of:

N-(1-hydroxy-2-ketopropyl)-methylpyroglutamate;

N-(1-hydroxy-2-ketopropyl)-butylpyroglutamate;

N-(1-hydroxy-2-ketopropyl)-benzylpyroglutamate;

N-(1-hydroxy-2-ketopropyl)-ethylpyroglutamate;

N-(1-acetoxy-2-ketopropyl)-methylpyroglutamate;

N-(1-acetoxy-2-ketopropyl)-butylpyroglutamate;

N-(1-acetoxy-2-ketopropyl)-benzylpyroglutamate; and

N-(1-acetoxy-2-ketopropyl)-ethylglutamate; or a pharmaceutically acceptable salt thereof.

9. The formulation according to claim 8, wherein the imino acid conjugate is in aqueous, solid or lyophilized form.

10. The formulation according to claim 8, in a dosage form is selected from the group consisting of a solution, syrup, a sachet, a hard gelatin capsule, a soft gelatin capsule and a tablet.

11. The formulation according to claim 8, wherein a unit dosage ranges from 60 mg to 18 gm.

12. The formulation according to claim 1, wherein a unit dosage ranges from 60 mg to 18 gm.

13. A method for treating cancer of the lung, colon, pancreas, oral, prostate, glioblastoma or lukemia comprising administering a formulation of imino acid conjugate according to claim 9 to a patient in need thereof.

14. A method of treating cancer according to claim 13, by administering a formulation of the imino acid conjugate in the range of 1 to 300 mg/kg body weight of the patient.

* * * * *